US00PP35165P2

(12) United States Plant Patent
Carruth

(10) Patent No.: US PP35,165 P2
(45) Date of Patent: May 16, 2023

(54) SHRUB ROSE PLANT NAMED 'WEKSWIPUFSTE'

(50) Latin Name: *Rosa hybrida*
Varietal Denomination: WEKswipufste

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/803,806

(22) Filed: Nov. 30, 2022

(51) Int. Cl.
*A01H 5/02* (2018.01)
*A01H 6/74* (2018.01)

(52) U.S. Cl.
USPC ..... Plt./102

(58) Field of Classification Search
USPC ..... Plt./102, 130, 141
CPC ... A01H 5/02; A01H 5/00; A01H 6/74; A01H 6/749
See application file for complete search history.

(56) References Cited

U.S. PATENT DOCUMENTS

| | | | | |
|---|---|---|---|---|
| PP5,975 P | | 5/1987 | Moore | |
| PP6,262 P | * | 8/1988 | Stephens | Plt./140 |
| PP13,449 P2 | * | 1/2003 | Carruth | A01H 5/02 Plt./102 |

* cited by examiner

*Primary Examiner* — June Hwu
(74) *Attorney, Agent, or Firm* — McKee, Voorhees & Sease, PLC

(57) ABSTRACT

A new variety of Shrub rose suitable for garden decoration, having flowers of magenta with lighter reverse coloration.

1 Drawing Sheet

Classification: The present disclosure relates to a new *Rosa hybrida* plant.

Variety denomination: The new plant has the varietal denomination 'WEKswipufste'.

BACKGROUND OF THE INVENTION

This invention relates to a new and distinct variety of Shrub Rose. It has as its seed parent the variety known as 'MORchari' (U.S. Plant Pat. No. 5,975) and a non-disseminated seedling of my creation as its pollen parent with the following genetic origin Wild Blue Yonder x [(Purple Heart x seedling) x Stephens' Big Purple (U.S. Plant Pat. No. 6,262, 'Stebigpu')]. It was hybridized by Thomas F. Carruth. It was hybridized by the inventor.

SUMMARY OF THE INVENTION

Among the features which distinguish the new variety from other presently available and commercial rose cultivars known to the Applicant are the following combinations of characteristics: its strong sweet grapefruit scent with overlaying fruity fragrance, its unusual magenta with lighter reverse flower coloration, its excellent color stability throughout the life of the flower and its large cluster composed of many flowers. The plant has a bushy rounded moderately spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKswipufste' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'MORchari' by the following combination of characteristics: whereas 'WEKswipufste' bears medium sized (about 5.6 to about 9.1 cm. in diameter) very double flowers (about 53 to 104 petals), 'MORchari' bears significantly smaller flowers (about 3.8 cm. in diameter) with lesser petalage (about 55 to 60 petals). The new variety has a bushy rounded moderately spreading somewhat low to medium height growing habit (about 75 to about 94 cm. in height), whereas the seed parent has a rounded spreading significantly shorter growing habit (about 30 to about 45 cm. in height).

The new variety may be distinguished from its pollen parent, a non-disseminated seedling of my creation by the following combination of characteristics: whereas 'WEKswipufste' bears very double flowers (about 53 to 104 petals) of magenta with lighter reverse coloration, the non-disseminated seedling bears semi-double flowers of purple & white striped coloration with significantly lesser petalage (about 25 to 35 petals). The new variety bears medium sized flowers (about 5.6 to about 9.1 cm. in diameter), whereas the pollen parent bears smaller flowers (about 4.8 to about 5.7 cm. in diameter).

COMPARISON WITH THE CLOSEST COMMERCIALLY AVAILABLE CULTIVAR

The new variety may be distinguished from its closest commercially available cultivar, 'WEKstephitsu' (U.S. Plant Pat. No. 13,449) by the following combination of characteristics: whereas 'WEKswipufste' bears very double flowers (about 53 to 104 petals) of magenta with lighter reverse coloration, 'WEKstephitsu' bears double flowers of magenta to lavender-blue coloration with significantly lesser petalage (about 41 to 53 petals). The new variety has a bushy rounded moderately spreading somewhat low to medium height growing habit (about 75 to about 94 cm. in height), whereas the closest commercially available cultivar has an upright to somewhat spreading significantly taller growing habit (about 125 to about 140 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3- to 4-year-old rose plants of the new variety grown outdoors in Wasco, Calif. in the month of November. Throughout this specification, color references and/or values are based upon The Colour Chart of The Royal Horticultural Society (2001) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural, and climatic conditions, as well as differences in conditions of light and soil.

FLOWER

The new variety sometimes bears its flowers singly, usually in clusters of two to sixteen or more per stem. Flowers may be borne in rounded to mostly pyramidal clusters on strong medium length stems (about 25 to about 40 cm.). The cluster ranges from about 6.0 to about 14.0 cm. in diameter. Outdoors, the plant blooms abundantly and nearly continuously during the growing season. The flowers have a strong sweet grapefruit scent with overlaying fruity fragrance.

BUD

The peduncle is about 2.7 to about 3.6 cm. in length, of average caliper (about 0.15 to about 0.35 cm. in diameter), and usually erect. It is almost entirely smooth, with some stipitate glands. Peduncle color is near 146C often heavily suffused, especially on the side exposed to the sun, with near 181A.

Before the calyx breaks, the bud is about 0.8 to about 1.4 cm. in diameter at the widest point, about 1.1 to about 2.1 cm. in length, and pointed to ovoid in shape. The surface of the bud bears between 5 to 12 foliaceous appendages with numerous stipitate glands, usually with slender entire foliaceous parts extending beyond the tip of the bud about ¼ of its length. Bud color is between 146A to 146B sometimes lightly suffused, especially on the side exposed to the sun, with near 181C.

The sepals are 5 per flower, about 1.7 to about 3.0 cm. in length and about 0.7 to about 1.0 cm. in width at the widest point. The outer surface color of the sepal is between 146A to 146B sometimes lightly suffused, especially on the side exposed to the sun, with near 181C. The outer surface of the sepal is somewhat smooth and bears between 0 to 5 foliaceous appendages with numerous stipitate glands. The inner surface color of the sepal is near 146C broadly bordered by near 155C. After the sepals open, the inner surface color is sometimes lightly suffused, especially on the area exposed to the sun, with between 181C and 181D. The inner surface of the sepal is covered and edged with fine wooly tomentum; sepal margins are entire and lined with many stipitate glands and hairs. The sepals are moderately permanent, and usually straight in shape with acute apices.

The receptacle of the flower is of medium length (about 0.7 to about 0.9 cm.) and average in caliper (about 0.6 to about 0.8 cm. in diameter). The receptacle is funnel in form. Its surface is very smooth with somewhat thick fleshy walls. The receptacle color is near 146A.

As the petals open (after the calyx breaks), the bud is about 1.6 to about 2.3 cm. in diameter at the widest point, about 1.9 to about 2.4 cm. in length and pointed to ovoid in form. The color of the under and upper surfaces of the newly opened petals is between 77C and 71B. At the point where the petal attaches, there is a moderately large zone of near 155B.

BLOOM

When fully open, the bloom ranges from about 5.6 to about 9.1 cm. in diameter. Petalage is very double with about 53 to 104 petals and about 5 to 21 petaloids irregularly arranged. When partially open, the bloom form is somewhat globular, and the petals are cupped with petal edges moderately reflexed inward. When fully open, the bloom form is more cupped to full, and the petals are loosely cupped to near flat with petal edges somewhat reflexed inward.

PETALS

The substance of the petals is moderately thin, with upper surfaces slightly shiny to satiny with under surfaces slightly shiny. The petals are about 4.0 to about 5.2 cm. in length and about 1.6 to about 2.2 cm. in width at the widest point. Petal margins are nearly entire often with an obcordate tip.

The outer petals are narrowly obovate in shape with apices somewhat rounded and sometimes slightly notched with one to two notches.

The inner petals are narrowly obovate to obelliptic in shape with apices somewhat rounded and sometimes slightly notched with one to two notches.

Petaloids are about 0.6 to about 2.3 cm. in length and about 0.3 to about 0.8 cm. in width at the widest point. Petaloids are irregularly shaped narrowly spatulate to gladiate with rounded apices.

NEWLY OPENED FLOWER

The under-surface color of the outer petals is between 77C and 71B. At the point where the petal attaches, there is a moderately large zone of near 155B. The upper surface color of the outer petals is near 71B. At the point where the petal attaches, there is a moderately large zone of near 155B.

The under-surface color of the intermediate petals is between 72B and 72A. The upper surface color of the intermediate petals is near 72A.

The under-surface color of the inner petals is between 71D and 71C. The upper surface color of the inner petals is near 71C.

The under and upper surface colors of the petaloids are similar in coloration to the upper and under surfaces of the inner petals.

The general tonality of the newly opened flower is between 72A and 71C.

THREE-DAY-OLD FLOWER

The under-surface color of the outer petals is between 84C and 72B. At the point where the petal attaches, there is a moderately large zone of near 155B. The upper surface color of the outer petals is near 72B. At the point where the petal attaches, there is a moderately large zone of near 155B.

The under-surface color of the intermediate and inner petals is near 75A, darker at the petal edges to between 72B to 72C. The upper surface color of the intermediate and inner petals is between 72B and 72C.

The under and upper surface colors of the petaloids are similar in coloration to the upper and under surfaces of the intermediate and inner petals.

The general tonality of the three-day-old flower is between 72B and 72C.

On the spent bloom, the petals usually drop off cleanly.

In November in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 40) and are arranged regularly about the pistils; a few are mixed with petaloids. The filaments are medium to long length (about 0.8 to about 1.0 cm.) most with anthers. Filaments are near 4D in color. The anthers are of medium size for the class and all open approximately at the same time. Anther color when immature is near 15C on the external part and near 13D on the internal part. Anther color at maturity is near 22A on the external part and near 26A on the internal part. Pollen is somewhat sparse and near 165C in color.

FEMALE REPRODUCTIVE ORGANS

Pistils vary in number (average about 25). The styles are somewhat even, average to somewhat long in length (about 0.6 to about 0.9 cm.), average in caliper, and bunched to somewhat columnar. Stigma color is between 22B and 22C. Style color is near 61C near the stigma fading to near white (155C) at the base. Ovaries are usually all enclosed in the calyx. The ovaries are medium in size and 155A in color at the mature flower stage.

Hips have not been observed on this variety when grown in Wasco, Calif.

FOLIAGE

The compound leaves are usually comprised of three to seven leaflets and are borne abundantly. The five-leaflet leaves are about 8.8 to about 10.2 cm. in length and about 6.7 to about 7.8 cm. in width at the widest point, very leathery in texture on both sides, and moderately glossy in finish on the upper side and matte in finish on the underside. The leaves have a pinnate venation pattern. The terminal leaflets are about 3.1 to about 5.4 cm. in length and about 1.8 to about 2.8 cm. in width at the widest point, shaped ovate with acuminate to acute apices and round bases. Their margins are simply serrate.

The upper surface color of the mature leaf is between 139A and 146A. The under-surface color of the mature leaf is near 146A. The under and upper colors of the leaf veins on the mature leaf are similar in coloration to the upper and under surfaces colors of the mature leaf. The upper surface color of the young leaf is between 137C and 146C, sometimes with a thin margin on the leaf edge of near 178B. The under-surface color of the young leaf is near 146C, sometimes with a thin margin on the leaf edge of 178B. The under and upper colors of the leaf veins on the young leaf are similar in coloration to the upper and under surfaces colors of the young leaf.

The rachis is about 5.2 to about 7.8 cm. in length, about 0.1 to about 0.2 cm in width at the widest point, and rough. The upper side is moderately grooved with many stipitate glands on the edges of the grooves. The under side of the rachis is rough with few medium sized prickles. The rachis color is near 146C on the underside and near 139B on the upper side, sometimes lightly suffused on the young leaves with near 178B.

The stipules are about 1.2 to about 1.5 cm. in length and somewhat narrow (about 0.4 to about 0.6 cm.) with medium length straight points that usually turn out at an angle of more than 45 degrees and sometimes recurve toward the stem. The under and upper surface color of the stipule is between 146C and 146D. The upper and under surfaces of the stipules are smooth in texture.

The petiole is average in caliper and smooth. The upper side is shallowly grooved with few hairs and stipitate glands on the edges of the grooves. The under side of the petiole is smooth with few hairs and stipitate glands. The petiole is about 0.5 to about 1.2 cm. in length and about 0.1 to about 0.2 cm in width at the widest point. The petiole color is near 146C on the under side and near 139B on the upper side, sometimes lightly suffused on the young leaves with near 178B.

The plant displays an above average degree of resistance to powdery mildew (*Sphaerotheca pannosa*), downy mildew (*Peronospora sparsa*) and rust (*Phragmidium* sp.) and an average degree of resistance to black spot (*Diplocarpon rosae*) as compared to other commercial varieties grown under comparable conditions in Wasco, Calif. The plant's winter hardiness and drought/heat tolerance are yet to be determined.

GROWTH

The plant has a bushy rounded moderately spreading somewhat low to medium height growing habit (about 75 to about 94 cm. in height and about 75 to about 94 cm. spread at the widest point), with very full branching. It displays moderately vigorous growth, and the canes are of medium caliper for the class (about 1.0 to about 1.3 cm. in diameter at the widest point).

The color of the major stems is between 146C and 146B. The major stems are rough in texture, and they bear several large prickles that are about 0.4 to about 0.5 cm. in length. The large prickles are almost straight to hooked slightly downward with a medium length broad oval base; prickle color is near N199D. The major stem bears few small prickles of similar shape and coloration.

The color of the branches is between 146C and 146D. The branches are rough in texture, and they bear few large prickles which are of similar size and shape to the large prickles on the major stems; prickle color is near N199D. The branches bear many small prickles of similar shape and coloration.

The color of the new shoots is 146C, sometimes lightly suffused with between 178A to 178B. The new shoots are rough in texture, and they bear many large prickles which are of similar size and shape to the prickles on the major stems; prickle color is near N199D. The shoots bear few small prickles of similar shape and coloration.

I claim:

1. A new and distinct Shrub rose plant of the variety designated 'WEKswipufste' substantially as described and illustrated herein.

* * * * *

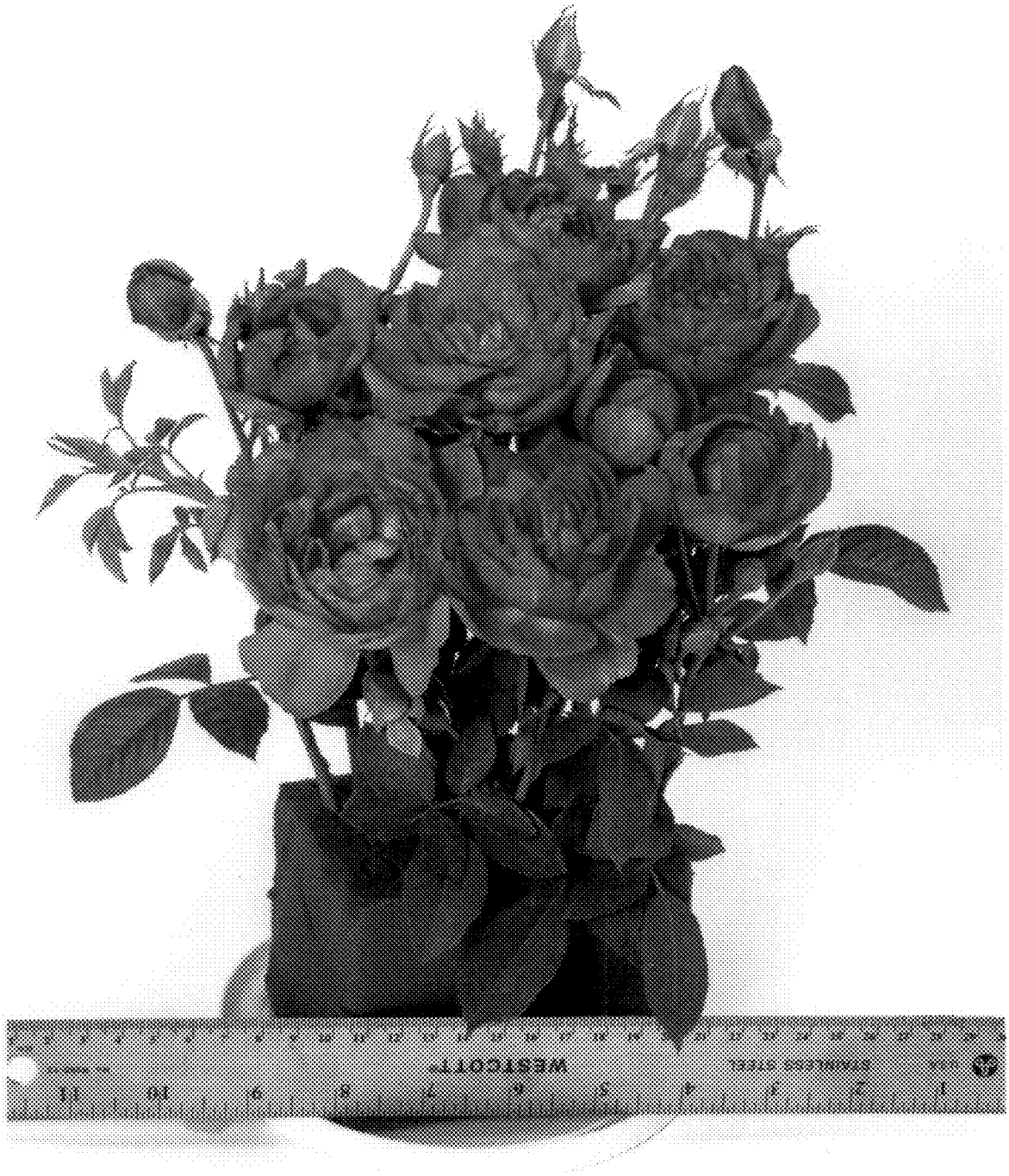
WESTCOTT